US00PP32558P2

(12) United States Plant Patent
Capo

(10) Patent No.: US PP32,558 P2
(45) Date of Patent: Dec. 1, 2020

(54) ***PETUNIA* PLANT NAMED 'KLEPH19412'**

(50) Latin Name: *Petunia hybrida*
Varietal Denomination: KLEPH19412

(71) Applicant: Klemm+Sohn GmbH & Co. KG, Stuttgart (DE)

(72) Inventor: Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/866,783

(22) Filed: May 5, 2020

(51) Int. Cl.
*A01H 6/82* (2018.01)
*A01H 5/02* (2018.01)

(52) U.S. Cl.
USPC ..... Plt./356.23

(58) Field of Classification Search
USPC ..... Plt./356.23
CPC ..... A01H 6/82; A01H 5/02
See application file for complete search history.

*Primary Examiner* — Annette H Para
(74) *Attorney, Agent, or Firm* — Weatherly IP Solutions, LLC; James Weatherly

(57) ABSTRACT

A new *Petunia* plant particularly distinguished by having red flower color with a compact and upright plant, is disclosed.

1 Drawing Sheet

Genus and species: *Petunia hybrida.*
Variety denomination: 'KLEPH19412'.

BACKGROUND OF THE NEW PLANT

The present invention comprises a new and distinct variety of *Petunia*, botanically known as *Petunia hybrida* and hereinafter referred to by the variety name 'KLEPH19412'. 'KLEPH19412' is a selection from a cross-pollination of the proprietary female *Petunia* line 'PHT-2012-3129' (unpatented) and the commercial male *Petunia* line 'Viva Bright Red' (unpatented).

In July of 2016, the proprietary female *Petunia* line 'PHT-2012-3129' and the male *Petunia* line 'Viva Bright Red' were cross pollinated in Latina, Italy and seeds were obtained. The seeds were sown and plants were grown for evaluation. A plant line was selected in April 2017 in Latina, Italy and named 'KLEPH19412'. In May 2017, 'KLEPH19412' was first vegetatively propagated by terminal tip cuttings and tissue culture in Latina, Italy. 'KLEPH19412' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Red flower color; and
2. A compact and upright plant.

DESCRIPTION OF THE PHOTOGRAPH

This new *Petunia* plant is illustrated by the accompanying photograph, which shows a close-up of the flower of the plant. The plant is about 16 weeks old grown in Stuttgart, Germany in June 2018. The colors shown are as true as can be reasonably obtained by conventional photographic procedures.

DESCRIPTION OF THE NEW VARIETY

The following detailed descriptions set forth the distinctive characteristics of 'KLEPH19412'. The data which define these characteristics were collected from asexual reproductions carried out in Latina, Italy. Data was collected on fourteen-week-old plants grown indoors in Latina, Italy under greenhouse conditions in March 2020. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH19412'.

Parentage:
- *Female.*—Proprietary *Petunia* line 'PHT-2012-3129'.
- *Male.*—Commercial *Petunia* line 'Viva Bright Red'.

Plant:
- *Form.*—Compact vigor.
- *Habit.*—Upright.
- *Height* (*from top of soil*).—Up to 15.0 cm.
- *Width* (*horizontal plant diameter*).—Up to 24.0 cm.
- *Propagation.*—Terminal tip cuttings.
- *Time to produce a finished flowering plant.*—12 to 14 weeks in winter under short day conditions, about 5 weeks in spring.
- *Time to initiate and develop roots.*—2 to 3 weeks.
- *Root description.*—Moderate density, moderate branching, white roots.

Stems:
- *Average number* (*basal*).—3.
- *Length of basal branches* (*from the base of the stem to the tip*).—About 16.0 cm.
- *Internode length.*—Up to 2.0 cm.
- *Diameter of branches* (*from midpoint*).—0.3 cm.
- *Stem color.*—RHS 144A to 144B.
- *Anthocyanin.*—Absent.
- *Texture.*—Pubescent.

Leaves:

*Arrangement*.—Slightly alternate along the stem, opposite under the inflorescence.

*Length*.—Up to 4.3 cm.

*Width*.—Up to 2.3 cm.

*Shape*.—Elliptic.

*Apex*.—Acute.

*Base*.—Attenuate.

*Margin*.—Entire.

*Immature leaf color*.—Upper surface: RHS N137D. Lower surface: RHS 138B.

*Mature leaf color*.—Upper surface: RHS N137B. Lower surface: RHS 138B.

*Texture*.—Upper surface: Pubescent. Lower surface: Pubescent.

*Venation pattern*.—Arcuate.

*Venation color*.—Upper surface: RHS N137D. Lower surface: RHS 138B.

*Petioles*.—Length: Up to 0.4 cm. Diameter: Up to 0.2 cm. Color: RHS 144C. Texture: Pubescent.

Flower bud:

*Shape*.—Irregularly oblong.

*Length*.—3.5 cm.

*Diameter*.—0.6 cm.

*Color at tight bud*.—RHS N77A.

*Texture*.—Pubescent.

Inflorescence:

*Blooming habit (flowering season)*.—Continuously flowering during spring and summertime.

*Inflorescence type*.—Sympodial, with monochasial growth.

*Number of flowers per node*.—1.

*Lastingness of individual blooms on the plant*.—About 11 days.

*Fragrance*.—Absent.

*Flowers*.—Arrangement: Composed of 5 fused petals. Diameter (flower face): Up to 7.5 cm. Depth (total length of flower): Up to 7.0 cm. Throat/Funnel: Length: Up to 3.0 cm. Diameter (at opening): Up to 1.2 cm. Texture: Inner surface: Smooth. Outer surface: Pubescent. Color: Inner surface: RHS 187B (dense veins of RHS 76D). Outer surface: RHS 178A. Petals: Color, mature flower (fully opened): Upper surface: RHS 46B with veins of RHS 187A. Lower surface: RHS 51B with RHS 187A main vein and RHS 187 B other veins. Apex: Emarginate. Base: Fused. Shape: Funnelform. Margin: Entire to slightly crenulate. Strength of waviness: Weak. Degree of lobation: Medium.

*Calyx arrangement*.—Whorl of 5 sepals, fused at the base. Sepals: Color: Upper surface: RHS N137D. Lower surface: RHS 137A. Length: Up to 1.6 cm. Width: Up to 0.6 cm. Shape: Oblanceolate. Apex: Acute. Base: Attenuate. Margin: Entire. Texture: Upper surface: Pubescent. Lower surface: Pubescent.

*Pedicels*.—Color: RHS 144A. Length: Up to 6.0 cm. Diameter: 0.2 cm. Texture: Pubescent.

Reproductive organs:

*Stamens*.—Quantity: 5. Shape: Needle with elliptic head. Filament: Length: Up to 1.4 cm. Diameter: About 0.05 cm. Color: RHS 158B. Anther: Shape: Elliptic. Color: RHS 158A. Length: 0.3 cm. Diameter: 0.25 cm. Pollen: Color: RHS 158A. Amount: Abundant.

*Pistils*.—Quantity per flower: 1. Length: Up to 2.5 cm. Stigma color: RHS 143C. Style color: RHS 154D.

Fruit and seed set: None observed.

Disease and pest/insect resistance: None observed.

COMPARISON WITH PARENTAL LINES AND KNOWN VARIETY

'KLEPH19412' is a distinct variety of *Petunia*. 'KLEPH19412' is distinguished from its parents as described in Table 1:

TABLE 1

Comparison with Parental Lines

| Characteristic | Variety 'KLEPH19412' | Female parent PHT-2012-3129 | Male Parent Viva Bright Red |
|---|---|---|---|
| Habit | Compact and upright | Medium compact and mounding | Medium vigor and trailing |

'KLEPH19412' is most similar to the commercial *Petunia* plant named 'KLEPH14248' (U.S. Plant Pat. No. 27,046). Differences between the two varieties are described in Table 2:

TABLE 2

Comparison with Similar Variety

| Characteristic | Variety 'KLEPH19412' | Commercial line 'KLEPH14248' |
|---|---|---|
| Vigour | Compact | Medium vigor |
| Plant habit | Upright | Semi-trailing |

I claim:

1. A new and distinct variety of *Petunia* plant named 'KLEPH19412' as illustrated and described herein.

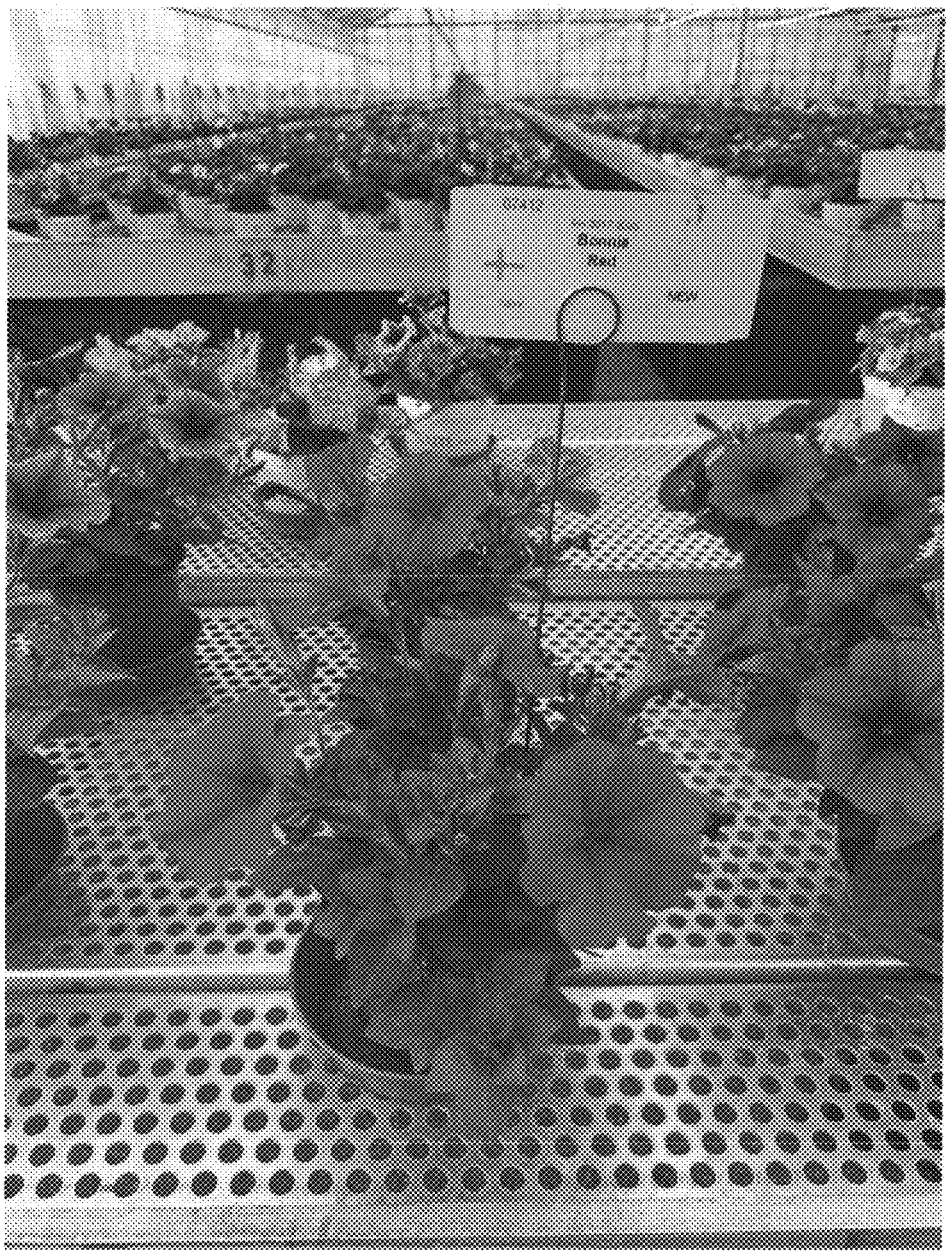

* * * * *